United States Patent [19]

Furler et al.

[11] 4,362,166
[45] Dec. 7, 1982

[54] DISPOSABLE MEDICAL PROBE AND CONNECTOR

[75] Inventors: Alan G. Furler, Glens Falls; Philip V. Stoddard, Greenwich, both of N.Y.

[73] Assignee: Mallinckrodt, Inc., St. Louis, Mo.

[21] Appl. No.: 204,048

[22] Filed: Nov. 4, 1980

[51] Int. Cl.³ .............................................. A61B 5/00
[52] U.S. Cl. ................................... 128/670; 128/715; 128/736; 128/773; 339/60 R; 339/186 R
[58] Field of Search ............... 128/642, 670, 671, 696, 128/700, 715, 784–789, 419 P, 773, 736; 339/60 R, 60 M, 117 R, 186 R, 186 M, 16 R, 16 C

[56] References Cited

U.S. PATENT DOCUMENTS

| | | | |
|---|---|---|---|
| 2,178,931 | 11/1939 | Crites et al. | 339/16 R |
| 3,287,031 | 11/1966 | Simmons et al. | 339/186 R |
| 3,333,045 | 7/1967 | Fisher et al. | 128/784 X |
| 3,416,533 | 12/1968 | Fisher et al. | 128/786 |
| 3,416,973 | 12/1968 | Benzinger | 136/235 |
| 3,525,068 | 8/1970 | Nelson | 339/117 R |
| 3,828,780 | 8/1974 | Morrison, Jr. | 128/275.1 |
| 3,951,136 | 4/1976 | Wall et al. | 128/642 |
| 4,073,287 | 2/1978 | Bradley et al. | 128/642 |
| 4,176,659 | 12/1979 | Rolfe | 128/635 |
| 4,176,660 | 12/1979 | Mylrea et al. | 128/671 |
| 4,304,239 | 12/1981 | Perlin | 128/642 |
| 4,304,240 | 12/1981 | Perlin | 128/642 |

FOREIGN PATENT DOCUMENTS

| | | | |
|---|---|---|---|
| 1440866 | 6/1976 | United Kingdom | 339/16 C |
| 721874 | 3/1980 | U.S.S.R. | 339/60 R |

OTHER PUBLICATIONS

"Body Tissue Transducer", IBM Technical Disclosure Bull., vol. 6, No. 8, Jan. 1964, pp. 13–14.

Primary Examiner—Lee S. Cohen
Attorney, Agent, or Firm—Bernard, Rothwell & Brown

[57] ABSTRACT

A disposable flexible medical device or probe and a reusable connector are provided. The disposable probe comprises a flexible tube of resilient plastic having a central major lumen and two or more minor lumens formed in the walls of the tube. Flexible electrically-conductive wires of undulating configuration extend through the minor lumens for conveying electrical signals from the distal end of the probe within the human body to suitable external monitoring instruments. The proximal end of the probe is formed as a female connector having longitudinally extending contacts on the inside surface of the major lumen, the contacts preferably being formed as an integral part of the wires extending through the minor lumens. A relatively rigid reusable male connector is employed as a coupling means. It includes transversely extending arcuate electrical contacts arranged for engagement with corresponding contacts on the female connector, the arcuate contacts being arranged on a tubular member surrounded by a spaced concentric sheath. It further includes a passage extending therethrough for coupling the major lumen of the disposable probe to an external stethoscope earpiece or other device. A key and slot arrangement is provided for insuring that the male and female connectors are connected in a properly polarized manner and a visible indicator is provided for facilitating such proper connection.

9 Claims, 6 Drawing Figures

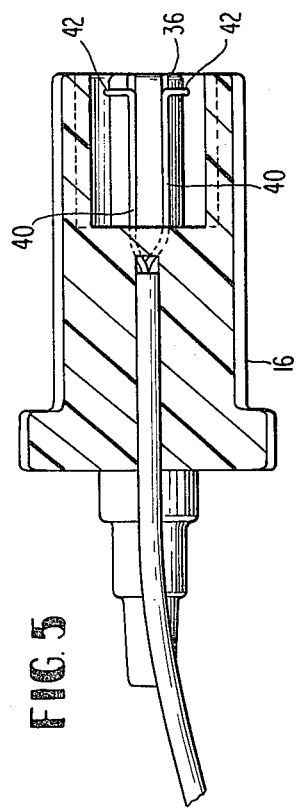
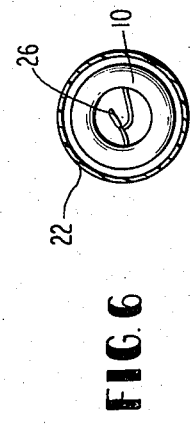
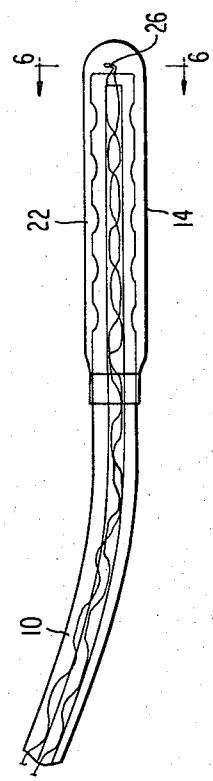
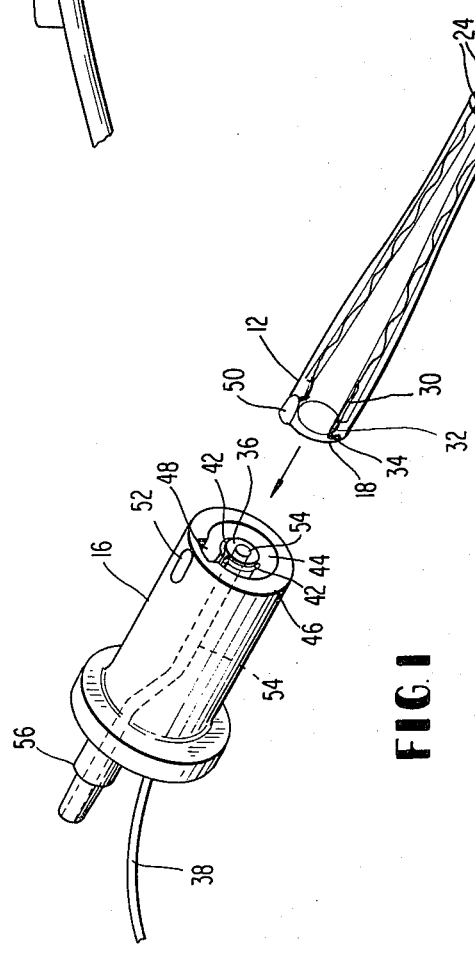
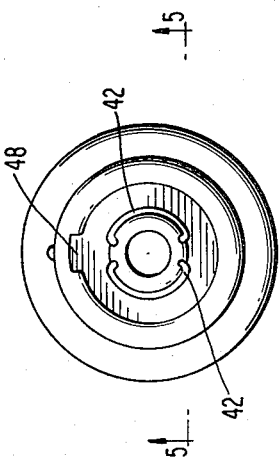
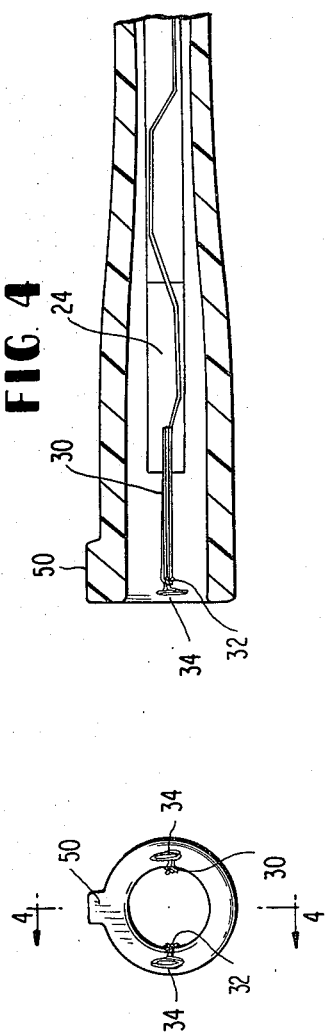

DISPOSABLE MEDICAL PROBE AND CONNECTOR

BACKGROUND OF THE INVENTION

1. Field of the Invention

This invention relates to disposable medical devices and, in particular, to disposable probes capable of simultaneous monitoring of multiple functions within a human body, and to connectors for connecting such disposable probes to suitable instruments.

2. Description of the Prior Art

Disposable medical probes have become an important part of modern medical practice, and flexible probes for monitoring a variety of conditions within the human body are widely employed. It is frequently necessary for a plurality of body functions to be monitored simultaneously by means of a single probe placed within a body cavity. In some cases one of these functions may be best monitored by electrical means associated with the probe, and another of these functions may be best monitored by some other physical phenomenon, such as sound. In other cases, it may be desirable that the probe provide both for monitoring a condition by means of electrical signals and for transmission of fluid to and from the patient.

There is a recognized need for reliable and economical disposable probes capable of monitoring such multiple body functions. The use of the disposable probes eliminates the costly and time-consuming sterilization procedures and also eliminates the risk of contamination which may result from improper or incomplete sterilization. Such disposable probes must not only be reasonably economical, but they must function fully and accurately for the duration of any medical procedure involved.

Various medical procedures for which probes are required, and particularly where disposable probes are desired, give rise to requirements that such disposable probes be easily and effectively connected with and disconnected from monitoring instruments with minimum risk of contamination of contacts and with assurance of good transmission of any electrical signals involved, that the probe be able to withstand extreme bending or stretching in any direction, that, where necessary, it provide excellent acoustical coupling with minimum interference by or with the electrical signals, and that, where necessary, it provide for unobstructed flow of fluid through the probe without interference with any of the other functions performed by the probe.

The prior art has disclosed a number of disposable probes which include provision for transmission of electrical signals and for transmission of sound or unobstructed flow of fluid. Such prior art probes have included provision for connecting the probe to suitable electrical or sound monitoring instruments.

Such prior art probes, however, have suffered from various defects which limit their achievement of the full range of objectives desired for disposable probes. For example, in some cases, they have failed to provide optimum flexibility along with sure transmission of electrical signals. In other cases, the arrangement provided for making connection to external instruments has required extreme care in order to assure good electrical connection, or has been unduly expensive, or has been constructed so as to have a risk of contamination of electrical contacts.

These deficiencies of the prior art have been overcome, and a disposable probe has been provided which includes a simple and effective connection for transmitting electrical signals to monitoring instruments, which assures that the contacts are clean and free of contamination, and which provides the requisite flexibility for internal use without sacrifice of the effective transmission of electrical and acoustic signals and transmission of fluid when required.

Accordingly, it is an object of this invention to provide a disposable probe and connector arrangement which is economical, which has a requisite flexibility for internal use in a variety of situations, which provides for simple and easy connection to external instruments, and which provides for maintaining clean electrical contacts and avoiding inadvertent contamination thereof.

SUMMARY OF THE INVENTION

In carrying out this invention, in one form thereof, there is provided a disposable flexible medical device or probe and a reusable connector. The disposable probe comprises a flexible tube of resilient plastic having a central major lumen and two or more minor lumens formed in the walls of the tube. Flexible electrically-conductive wires of crinkled or undulating configuration extend through the minor lumens for conveying electrical signals from the end of the probe within the human body to suitable external monitoring instruments. The proximal end of the probe is formed as a female connector having longitudinally extending contacts on the inside surface of the major lumen, the contacts preferably being formed as an integral part of the wires extending through the minor lumens. A relatively rigid reusable male connector is employed as a coupling means. It includes transversely extending arcuate electrical contacts arranged for engagement with corresponding contacts on the female connector, the arcuate contacts being arranged on a tubular element surrounded by a spaced concentric sheath. It further includes a passage extending therethrough for coupling the major lumen of the disposable probe to an external stethoscope earpiece or other device. A key and slot arrangement is provided for insuring that the male and female connectors are connected in a properly polarized manner and a visible indicator is provided for facilitating such proper connection.

DESCRIPTION OF THE DRAWINGS

In the following description, reference is made to the accompanying drawings in which:

FIG. 1 is a perspective view of the multipurpose medical probe and connector of this invention;

FIG. 2 is an end view of the male connector;

FIG. 3 is an end view of the proximal end of the disposable probe, illustrating the end portion of the female connector;

FIG. 4 is an enlarged longitudinal sectional view of the proximal end of the probe, taken along the line 4—4 in FIG. 3;

FIG. 5 is a sectional view of the male connector, taken along the line 5—5 in FIG. 2; and FIG. 6 is a sectional view of the distal end of the probe taken along the line 6—6 in FIG. 1.

DESCRIPTION OF THE PREFERRED EMBODIMENT

Referring to FIG. 1, there is shown one embodiment of the disposable probe and connector arrangement of this invention. As there shown, the device includes a disposable probe 10, having a proximal end 12 and a distal end 14, which is adapted to be inserted into the human body. The particular probe illustrated is an esophageal probe, but it will be apparent as the description proceeds that the device is suitable, with appropriate modification, for other internal uses. The device further includes a relatively rigid male connector 16 which is constructed so as to mate with a female connector 18 disposed at the proximal end of the disposable probe 10.

The probe, in the form shown, is a flexible tubular member preferably formed from a suitable flexible plastic material such as polyvinyl chloride. The tubular member includes a major central lumen 20 which extends the full length of the tubular member from the proximal end to the distal end thereof. In the form shown, the distal end of the probe is enclosed by a cuff 22.

The probe further has formed within the walls thereof two spaced minor lumens 24 which extend from a point near the proximal end of the probe to a point near the distal end of the probe. In the form shown, the disposable probe includes a temperature-sensing element 26, which may be any suitable thermocouple or thermistor, disposed at the distal end. Electrical conductors 28 are connected to the temperature-sensing element 26 and the minor lumens 24 provide paths for the conductors to the proximal end of the disposable probe. Since the probe is to be inserted into the human body, in the specific case shown through the mouth, to monitor internal conditions, it must necessarily be highly flexible and may in some cases encounter reasonably severe bending which could place a strain on one or the other or both of the conductors depending upon the direction of the bending. In order to minimize any such strain, the minor lumens 24 have a cross sectional area substantially greater than that of the conductors 28, and the conductors 28 are formed, as shown in FIG. 1, in an undulating form so that the length of each conductor exceeds significantly the length of the lumen within which it is contained. This undulating formation of the conductors provides for stretching of the conductors in the case of bending of the probe and thereby eliminates any adverse effect on the conductors from such bending. The term "undulated" in the description and claims is intended to include a variety of configurations, such as crinkled, sinuous, etc. by which it can be insured that the conductors have a significantly greater length than that of the lumens within which they are placed. Placing the conductors 28 internally of the wall of the probe within the minor lumens eliminates any need to provide insulation on the conductors 28.

In order to provide for electrical connection to the male connector 16, the conductors 28, pulled through the minor lumens 24 near the proximal end of the probe 10, are formed into loops. The ends are then reinserted into the minor lumens 24 and extended through the wall of the probe into the major lumen 20. As shown in FIGS. 1 and 3, the conductors are arranged to run longitudinally in exposed fashion along the wall of the major lumen to provide spaced contacts 30. The conductor ends are then pulled through the loops formed previously and knotted or tied to fix the contact positions. The knot 32 which is formed may be caused to be embedded in the surface of the plastic wall by a heat molding process also used to shape the proximal end of the probe. Particularly if a single loop knot is used, the conductors may be extended into the wall of the probe toward the proximal end thereof and formed into a plurality of wraps 34 extending transversely of the probe and embedded in the plastic which forms the wall of the probe. A firm anchor is provided for the ends of the conductors.

It will be noted from the above description that the contacts 30 are positioned internally of the probe on the wall of the major lumen 20. Therefore, when the probe is being handled, for example when being mated with the male connector 16, there is no risk of the user's hands coming into contact with the contacts 30. Hence any risk of contamination of these areas is completely avoided. Since the electrical signals to be transmitted may be very small, it is important that the contacts be clean and free of even minimal contamination. Such contamination could increase resistance and encourage active corrosive processes leading to the generation of spurious voltages. By the above construction, this desired condition is assured.

In order to provide for conducting of the electrical signals from the disposable probe to a suitable external monitoring instrument, the male connector 16 is provided. The male connector 16 is intended to be reusable and is formed of a relatively rigid plastic material. It includes a central tubular member 36 which is adapted to be received within the female connector at the proximal end of the probe 10. The male connector 16 includes an electrical lead 38 extending therefrom and adapted to be connected to an electrical monitoring instrument, not shown. The electrical lead 38 extends through a passage in the body of the connector 16 and includes two electrical conductors 40 which extend along the outer surface of the tubular member 36. In order to provide contacts for engaging corresponding contacts 30 of the female connector, each of the conductors 40 is formed, near the entrance of the male connector, into an arcuate shape extending circumferentially of the tubular member 36, as shown at 42. Because of the arcuate arrangement of the contacts 42 which is transverse of the longitudinally extending contacts 30 of the female connector, engagement of the contacts 30 and 42 is assured. Moreover, it can be seen that in assembling the female connector of the disposable probe with the male connector, it is necessary that a significant relative movement of the contacts 30 and 42 take place. This insures that any film on these contacts resulting from oxidation is removed and excellent electrical contact is obtained. It is important that any resistance at the contacts be minimized since the device involved may utilize very small electrical signals.

The tubular member 36 is disposed within a recess 44 provided by a surrounding concentric sheath 46 which forms the outer wall of the male connector 16. Because of this construction, the contacts 42, like the contacts 30, are protected against inadvertent contact with the hands of the user during assembly or disassembly of the male and female connectors, thereby providing further avoidance of any risk of contamination of the contacts.

In order to insure that the conductors 28 and the conductors 40 are connected with the right polarity, provision is made for positive orientation of the probe 10 with respect to the male connector 16. In the particular form shown, a recess or keyway 48 is provided in the inner wall of the sheath 46 of the male connector, and a cooperating projection or tab 50 is provided on the female connector. In order to connect the male and female connectors, it is therefore necessary to align the projection 50 with the keyway 48, thereby insuring the proper orientation of the two parts. In order to facilitate quick and easy assembly, a projection 52, or other indicating mark, is provided on the outer wall of the male connector 16 directly above the keyway 48. It can be seen, therefore, that when the probe 10 and the connector 16 are held in the hands in a normal manner, the user, looking down from above, can readily align the projection 50 with the projection 52 visually and can easily insert the probe in the proper orientation.

Since it is intended that the device of this invention be also usable for monitoring sound by means of a stethoscope, the male connector 16 is formed with a generally central passage 54 extending therethrough. A tubular projection 56 communicating with the passage 54 is provided at one end of the connector 16 for receiving a stethoscope. In the assembled position, the passage 54 is in registry with the major lumen 20 of the probe 10, thereby providing communication between the distal end of the probe and a stethoscope connected at the tubular projection 56.

From the above description, it will be apparent that the disposable probe and reusable connector arrangement of the present invention provides a device which satisfies all the requirements for utilization in the environment and for the purpose for which it is intended. The electrical conductors are provided within enclosed passageways or minor lumens within the probe and are formed so as to be able to withstand even severe bending. The contacts of the disposable probe are easily and economically formed and the contacts of both the probe and the male connector are positioned so as to be protected from any inadvertent contamination by the user in the handling of the components of this device.

While a particular embodiment of this invention has been shown and described, it will be apparent that modifications of the device may be made without departing from the spirit and scope of the invention. For example, while the device has been shown specifically in connection with an esophageal probe having a membrane covering the distal end, it can equally be employed, with appropriate modification, as a tracheal probe providing fluid communication between the distal end of the probe and any suitable component external of the device, while still preserving the multiple functions of the device. Also while a temperature-sensing element has been shown connected to the probe conductors, these conductors could be connected to other devices at the distal end for transmitting electrical signal indicative of other internal conditions. Accordingly, it is intended by the appended claims to cover all modifications which come within the spirit and scope of this invention.

It is claimed:

1. A probe and connector comprising:
   (a) a disposable probe including a flexible tubular member having a central major lumen, said probe including a distal end and a proximal end;
   (b) a condition-sensing element disposed at said distal end;
   (c) a plurality of flexible conductors electrically connected to said sensing element, each of said conductors extending from said distal end to said proximal end of said probe;
   (d) the proximal ends of said conductors being disposed on the inner wall of said tubular member to form first contacts near the proximal end thereof;
   (e) said proximal end of said probe being formed to provide a female connector;
   (f) a relatively rigid reusable male connector having a plurality of second conductors extending therethrough and adapted to be connected to an indicating instrument, the ends of said second conductors being disposed on said male connector to form second contacts, said male connector being removably connected to said female connector with said second contacts engaging respective ones of said first contacts;
   (g) said first and second contacts being slidably movable relative to each other during engagement and disengagement thereof; and
   (h) said first contacts extending in a direction transverse of said second contacts, whereby the sliding movement during engagement and disengagement of said first contacts and said second contacts insures wiping action for removing any contamination from said contacts and achieving excellent electrical conduction.

2. The probe and connector of claim 1 wherein:
   (a) said first contacts extend longitudinally of said female connector; and
   (b) said second contacts extend transversely of said male connector;
   (c) whereby wiping action of said first and second contacts is insured during connection of said female and male connectors.

3. The probe and connector of claim 2 wherein each of said first contacts comprises a wire extending longitudinally within said probe, the ends of said wires forming said first contacts being heat-embedded in the wall of said major lumen.

4. The probe and connector of claim 3 and further including a second tubular member registering with said central lumen of said probe to provide communication between said second tubular member and the distal end of said probe; and wherein
   said male connector further includes a tubular projection extending from one wall thereof and adapted for connection to a stethoscope earpiece, said tubular projection communicating with said second tubular member to provide for sound transmission from said distal end of said probe to the stethoscope earpiece.

5. The probe and connector of claim 1 wherein:
   (a) said male connector includes a relatively rigid second tubular member, said second contacts being disposed on the exterior surface of said second tubular member; and
   (b) said male connector further includes a sheath concentric with said second tubular member extending beyond said second contacts;
   (c) said female connector being received between said second tubular member and said sheath.

6. The probe and connector of claim 5 wherein said second contacts are of arcuate form and extend circumferentially of said second tubular member along portions of the exterior surface thereof.

7. The probe and connector of claim 5 wherein said sheath and said female connector include a cooperating projection and recess to insure correct orientation of said male and female connectors to obtain proper polarization.

8. The probe and connector of claim 7 wherein said recess is on the inner wall of said sheath and said projection is on the exterior surface of said female connector.

9. The probe and connector of claim 8 wherein said sheath includes on its exterior surface a projection circumferentially aligned with said recess to facilitate alignment of said male and female connectors.

* * * * *